(12) United States Patent
Gao et al.

(10) Patent No.: US 7,039,528 B2
(45) Date of Patent: May 2, 2006

(54) METHOD FOR DETECTING LEAK BEFORE RUPTURE IN A PIPELINE

(75) Inventors: Ming Gao, Houston, TX (US); Sergio Limon, Houston, TX (US)

(73) Assignee: General Electric Company, Schenectady, NY (US)

( * ) Notice: Subject to any disclaimer, the term of this patent is extended or adjusted under 35 U.S.C. 154(b) by 7 days.

(21) Appl. No.: 10/710,702

(22) Filed: Jul. 29, 2004

(65) Prior Publication Data

US 2006/0025937 A1   Feb. 2, 2006

(51) Int. Cl.
*G01B 3/34* (2006.01)
*G01B 5/28* (2006.01)

(52) U.S. Cl. .......................................... 702/35; 702/34

(58) Field of Classification Search ................... 702/35, 702/34; 404/72, 75
See application file for complete search history.

(56) References Cited

U.S. PATENT DOCUMENTS 5,496,130 A * 3/1996 Tschegg ........................ 404/75

* cited by examiner

*Primary Examiner*—John Barlow
*Assistant Examiner*—Meagan S Walling
(74) *Attorney, Agent, or Firm*—Cantor Colburn LLP

(57) ABSTRACT

A method for leak-before-rupture assessment including using a failure assessment diagram (FAD) assessment curve from a crack initiation based FAD analysis to analyze a crack in a material; and using a ductile tearing analysis in conjunction with the FAD assessment curve to detect a crack exhibiting at least one of ductile tearing stability and tearing instability prone to rupture during growth of the crack.

19 Claims, 4 Drawing Sheets

Material JR Curve

Through thickness cracks
Critical size for tearing instability = 4.9"

Surface Cracks (90% wt)
Critical size for tearing instability > 5"

US 7,039,528 B2

METHOD FOR DETECTING LEAK BEFORE RUPTURE IN A PIPELINE

BACKGROUND OF THE INVENTION

This invention relates to a method for detecting a leak before rupture, and more particularly, relates to a method for detecting a leak before rupture using a tearing instability approach in pipeline applications.

Cracks or crack fields can initiate and grow in a pipeline by stress corrosion cracking, fatigue, or corrosion fatigue. The pipeline leaks if one of the cracks penetrates through the wall. The prompt detection of the leak can serve as an early warning and remedial actions can be taken to avoid a subsequent catastrophic failure. It is practically important, therefore, to develop analysis methods that predict conditions for a "leak-before-rupture".

The first incident of external stress corrosion cracking (SCC) on natural gas pipelines occurred in the mid 1960's and hundreds of failures have occurred since that time. Stress corrosion cracking (SCC) is the formation of brittle cracks in a normally sound material through the simultaneous action of a tensile stress and a corrosive environment.

Evaluation of leak-before-rupture for crack containing pipelines is an area that needs to be addressed for integrity assessment. Currently, fracture mechanics based industry standards, such as API 579-2000, provide detailed procedures for leak-before-rupture assessment using a Level I or III Failure Assessment Diagram (FAD) analysis. Since these procedures only predict crack initiation rather than a catastrophic failure for materials that exhibit stable crack growth by ductile tearing, the results are inconsistent with leak incidents observed in the field.

The criteria for a leak before rupture require that (1) the largest initial crack size left in the structure (e.g., pipeline wall) will not lead to fracture during the life of the component and (2) the largest length of a through-wall crack is less than that which catastrophic rupture will occur for all applicable load cases using either a Level II or Level III FAD assessment method. However, the FAD procedures for critical size analysis, i.e., the largest acceptable crack size, in API 579 is not consistent with crack initiation criteria in references such as, I. Milne, R. A. Ainsworth, A. R. Dowling and A. T. Stewart: "Assessment of integrity of structures containing defects", CEGB report R/H/R6—Revision 3, 1986; and M. Janssen, J. Zuidema and R. J. H. Wanhill: "Elastic-Plastic fracture mechanics", *Fracture Mechanics*, Part III, Chapter 8, pp. 198–203, Delft University Press (2002).

FAD procedures in API 579 for critical size analysis is more appropriate when material failure is expected to be either brittle or is preceded by only a limited amount of ductile tearing. For materials exhibiting significantly ductile tearing prior to failure, prediction of leak or rupture conditions is conservative and does not provide consistent results with field observed "leak-before rupture" incidents. This is because the resulting increase in toughness involved during crack growth is not taken into account in the analysis.

Accordingly, there is a need for a method for detecting a leak before rupture that accounts for the contribution of significant ductile tearing that provides a more accurate prediction by taking into account an of increase in the material fracture toughness involved during crack growth by a ductile tearing mechanism.

BRIEF DESCRIPTION OF THE INVENTION

The above discussed and other drawbacks and deficiencies are overcome or alleviated in a method of detecting a leak-before-rupture using a ductile tearing and tearing instability approach in pipeline applications.

In an exemplary embodiment, a method for leak-before-rupture assessment including using a failure assessment diagram (FAD) assessment curve from a crack initiation based FAD analysis to analyze a crack in a material; and using a ductile tearing analysis in conjunction with the FAD assessment curve to detect a crack exhibiting at least one of ductile tearing stability and tearing instability prone to rupture during growth of the crack.

In another embodiment, a method to detect leak-before-rupture cracks in a pipeline material that exhibits stable crack growth by ductile tearing includes using a failure assessment diagram (FAD) assessment curve from a crack initiation based FAD analysis to analyze a crack in a material; and using a ductile tearing analysis in conjunction with the FAD assessment curve to detect a crack exhibiting at least one of ductile tearing stability and tearing instability prone to rupture during growth of the crack, wherein the ductile tearing analysis takes into account an increase in a material fracture toughness during the crack growth.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several Figures.

DETAILED DESCRIPTION OF THE INVENTION

The acceptance criteria for a crack-containing structure in accordance with the API 579 assessment procedures and associated assessment procedures, such as, R6 and BS 7910, is analyzed against the initiation of crack extension rather than crack instability (rupture). Since ductile materials in a plane stress loading condition (e.g., thin wall for linepipe ferrite steels on the upper shelf of a ductile-brittle transition curve) often exhibit extensive plastic deformation prior to rupture, the assessment methodology in such a case can be extremely conservative and may not be appropriate for predicting actual failure conditions like leak-before-rupture.

Figure 1:
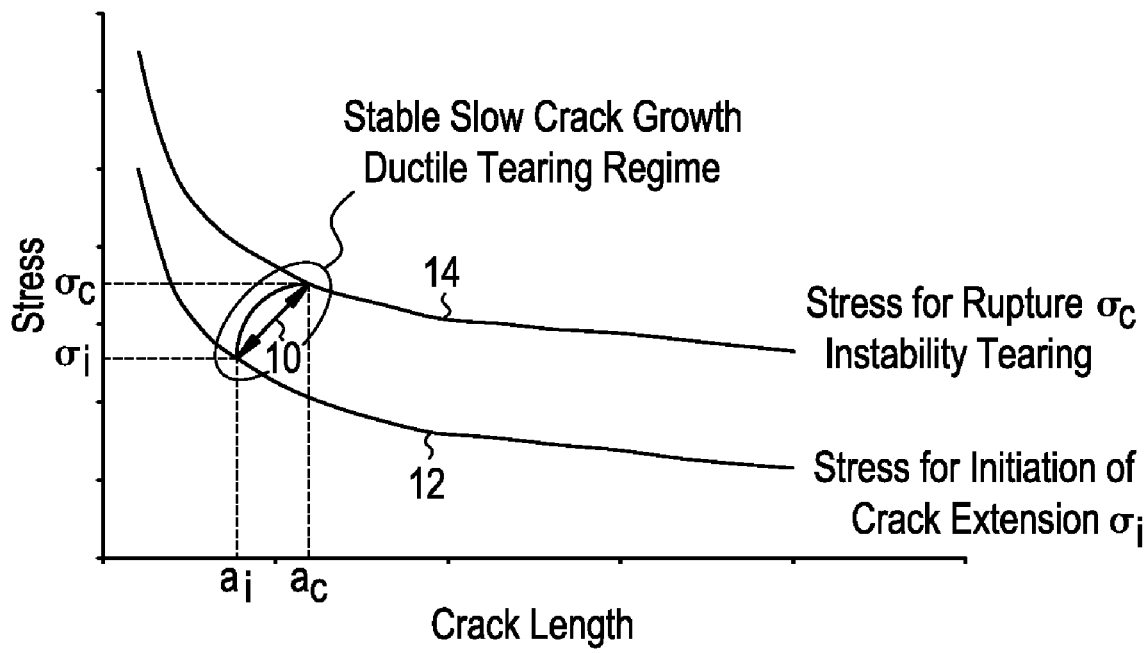
FIG. 1 is a graph of stress versus crack length illustrating slow crack growth in a plane stress condition for ductile materials.

To develop a tearing instability model for leak-before-rupture assessment, the ductile tearing and tearing instability process is reviewed. This process is graphically illustrated in FIG. 1, where a crack with an initial length a begins to extend at $\alpha_i$ (e.g., initiation of crack growth) at a certain stress $\sigma_i$. If the stress is maintained at $\sigma_i$, no further crack growth occurs at this stress because G=R where G is the driving force and R is the material resistance to crack extension. A slight increase in the stress is then required for an additional crack extension, however, the crack remains stable because a new balance of G=R is established again after the increment of stress. While this process continues, stable crack growth proceeds in a region 10 between a first stress curve 12 and a second stress curve 14 accompanied with increasing stress until a critical combination of stress $\sigma_c$ and crack length $\alpha_c$ is reached at the second curve 14. At this point, instability of crack growth occurs. The first curve 12 represents stress for initiation of crack extension $\sigma_i$, while second curve 14 represents critical stress $\sigma_c$ for rupture instability tearing. The region 10 between first an second curves represents a stable slow crack growth ductile tearing region.

Figure 2:
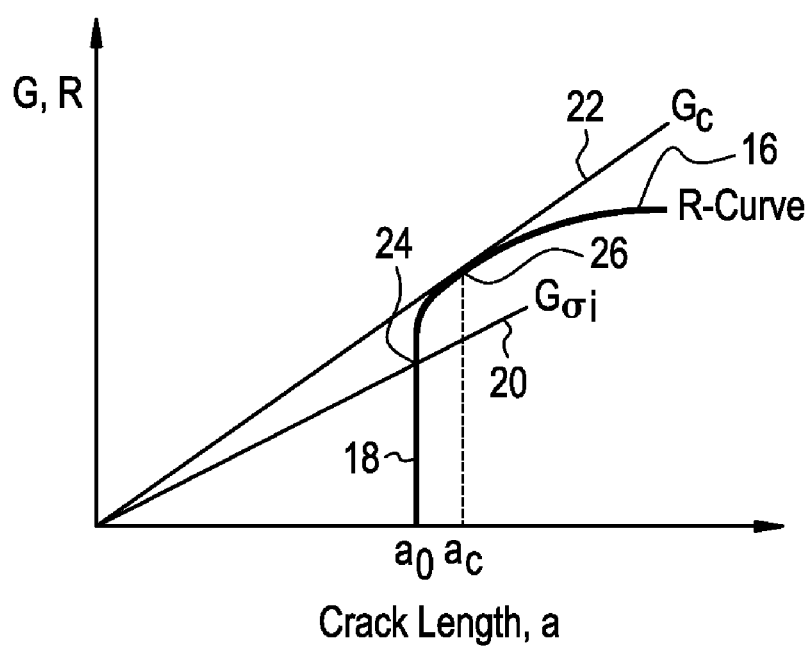
FIG. 2 is a typical R-curve illustrating conditions for crack extension initiation and tearing instability (rupture)

The ductile tearing and tearing instability process may be more clearly described using an R-curve concept referring to FIG. 2. A material resistance to crack extension is depicted as a rising curve 16, i.e., R-curve, with a vertical segment 18 corresponding to a no crack extension at a low stress level (i.e., low driving force G). The driving force G for crack extension is depicted as straight lines 20 and 22 (i.e., G-lines $G_{\sigma i}$ and $G_c$) through the origin of the coordinates. At a stress level of $\sigma_i$, crack extension initiates, as indicated by an intersection point 24 of the $G_{\sigma i}$ line 20 and the R-curve 16. At this stress level, further crack extension cannot occur because G line 20 is inside R-curve 16, i.e., $G_{\sigma i}$<R. Further extension can occur only when $G_\sigma$ becomes slightly higher than $R_i$ following the R-curve, and the stable growth condition is maintained at each increment of $G_\sigma$. This slow crack growth by ductile tearing proceeds stably until $\sigma_c$ and $\alpha_c$ are reached at an intersection point 26 of the $G_c$ line 22 and R-curve 16. Beyond this point 26, $G_\sigma$ becomes greater that R, as indicated by the $G_c$ line 22, and instable tearing (i.e., rupture) occurs.

Therefore, the conditions for instable tearing are expressed as:

$$G_\sigma > R_\sigma \quad (1)$$

and $$\frac{\partial G_\sigma}{\partial a} > \frac{\partial R_\sigma}{\partial a} \quad (2)$$

For ductile materials in plane stress conditions, it is now generally accepted by those skilled in the pertinent art that the J-integral and the Crack Opening Displacement (COD) approaches provide a proper description of elastic-plastic fracture behavior, which usually involves stable crack growth. In this disclosure, only the J-integral approach is employed. The J-integral is widely accepted as a measure of elastic-plastic fracture toughness of engineering alloys. The driving force for crack extension and the material resistance to crack growth are expressed as J app and $J_{mat}$, respectively.

Figure 3:
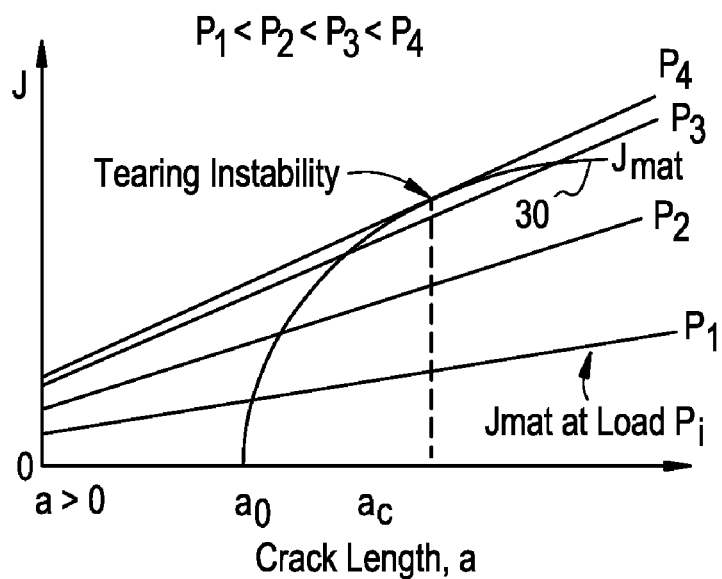
FIG. 3 is a graph of $J_{app}$ versus crack extension length illustrating a J-R curve in conjunction with various driving forces.

Referring now to FIG. 3, the R-curve 16 of FIG. 2 is now established in terms of $J_{mat}$ versus crack length extension (a) in a J-R curve 30, and the driving force for crack extension is expressed as $J_{app}$. The tearing instabilapp ity criteria are then expressed as:

$$J_{app} > J_{mat} \quad (3)$$

and $$\frac{\partial J_{app}}{\partial a} > \frac{\partial J_{mat}}{\partial a} \quad (4)$$

The above approach then serves as the basis for developing a criterion for leak-before-rupture assessment discussed more fully below.

The FAD curve based on R6, API 579, or BS7910 and associated procedures is widely used to assess the acceptance of crack-like features present in structures. If the assessment point is disposed outside the safe region of the FAD based on the crack initiation criterion, the crack is not acceptable. However, this does not always indicate a failure condition. For materials that exhibit stable crack growth by ductile tearing, the fracture toughness increases with crack growth. Similar to equations (3) and (4) above for tearing instability, the crack will remain stable as long as:

$$J_{app} \leq J_{mat} \text{ and } \frac{\partial J_{app}}{\partial a} \leq \frac{\partial J_{mat}}{\partial a} \quad (5)$$

To demonstrate how a crack remains stable, a ductile tearing analysis is performed by calculating Lr and Kr for a range of postulated crack extensions, $\Delta\alpha$, starting from the initial crack length $\alpha_o$, where Kr is $K_r$, a ratio of applied J-integral to material fracture toughness $$\sqrt{J_{app}/J_{mat}}.$$

Figure 5:
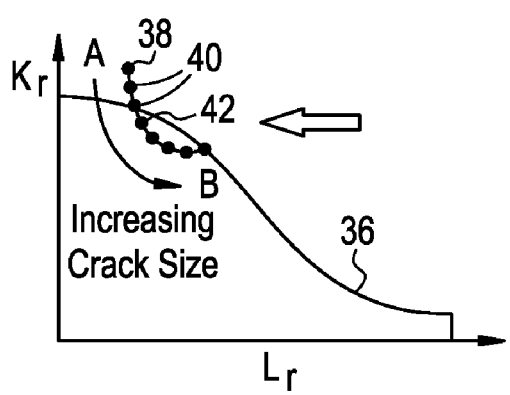
FIG. 5 is a failure assessment diagram (FAD) for a ductile tearing and tearing instability analysis using $J_{mat}$ derived from the J-R curve of FIG. 4 in accordance with an exemplary embodiment.
Figure 6:
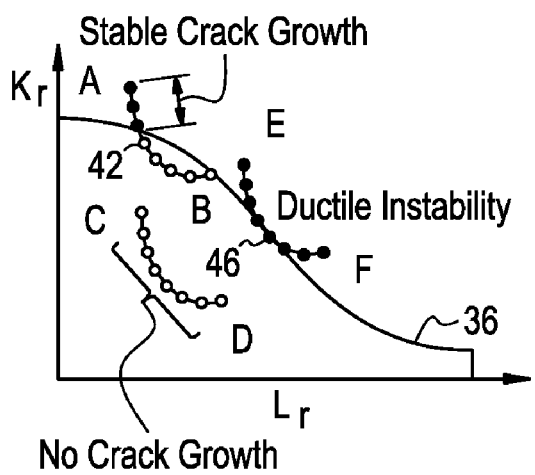
FIG. 6 is another failure assessment diagram (FAD) for a ductile tearing and tearing instability analysis illustrating stable crack growth as in FIG. 5, no crack growth, and ductile instability in accordance with an exemplary embodiment.

Referring now to FIGS. 5 and 6, the x-axis of FAD 36 is defined as the stress ratio $L_r$, (or, plastic collapse ratio), which is a ratio of reference stress $\sigma_{ref}$ (a function of applied stress and crack size) to yield strength $$\sigma_{ref}/\sigma_y$$

Figure 4:
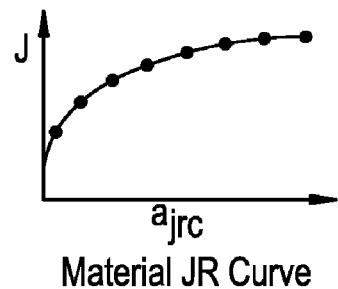
FIG. 4 is a typical material J-R curve illustrating eight assessment points.

The $J_{mat}$ is derived from the material's J resistance (J-R) mat curve of FIG. 4 for a crack growth increment $\Delta\alpha$. $J_{app}$ is calculated based on the applied load and the shape of the structure and crack geometry. Under constant load and temperature conditions, and for a single crack, an initial assessment point 38 is initially outside of the FAD 36 in FIG. 5. As a result of crack extension, both $$\sqrt{J_{app}} \text{ and } \sqrt{J_{mat}}$$

will increase. However, as long as inequality of equation (5) holds, $K_r$ will decrease. At the same time, $L_r$ will increase somewhat as a result of crack growth, therefore, the locus of assessment points 40 in the FAD 36 will be directed roughly downwards, see Curve AB, from the point 38 corresponding to an initial crack length $\alpha_o$, in FIG. 5.

FIGS. 5 and 6 also show that an assessment point 42 eventually drops below the assessment curve 36 as a result of ductile tearing and thus crack extension would eventually stop indicated by the nonfilled assessment points under FAD 36 in FIG. 6. For these cracks, even though they initiate outside the assessment curve 36 and exhibit some degeree of stable crack extension, the cracks do not result in failure by rupture at the operating pressure, implying that the crack is stable and acceptable in terms of failure by rupture even though a certain amount of crack increment has occurred.

On the basis of above analysis, two situations are recognized with respect to Curve AB: First, if the crack in FIG. 5 is a through-wall crack, a leak is expected because the assessment points eventually dropped below the assessment curve 36, indicating that the crack is stable and will not cause rupture even though the assessment point 38 is initially outside the FAD assessement curve 36. Second, if the crack is a surface crack, the crack may penetrate through the wall at a constant applied load, resulting in a leak due to stable crack extension if the crack is relatively deep and the crack extension is predominantly in the through-wall direction.

Referring now to FIG. 6, two more examples are illustrated for completeness of analysis. Curve CD is disposed entirely below the assessnment curve 36 and thus, no crack extension occurs at the applied load. Curve EF initiates above curve 36 and then becomes tangent to the assessment curve 36 at tangent point 46, which means that the load level for this particular crack is the limiting case. Any load greater than this load would result in a catastrophic failure. On the contrary, any load smaller than this load the assessment point 46 would eventually drop below the assessment curve 36 as a result of ductile tearing and crack growth would stop. The crack would leak if the crack was or had become a through-wall crack instead of rupturing.

It will be recognized that the above analysis considers ductile tearing due to application of a certain load only. It is assumed that no form of subcritical crack growth is involved during the tearing. If these crack growth mechanisms cannot be excluded, this analysis should only be applied to overload conditions. Obviously, subcritical crack growth under normal operating pressure should be taken into account to estimate the crack size after a certain service time and should be used for life cycle calculation based on subcritical crack growth rate and the critical size estimated from tearing instability based analysis.

Furthermore, it is evident that aJ-R relationship should be establised experimentally for the material containing crack-like features at the assessment temperature for performing tearing instability analysis.

Two field examples are presented below to validate the effectiveness of the tearing instability appproach for leak-before-rupture assessment described above. First, a small leak was found in a joint of a 16 inch O.D. pipeline due to a through-wall SCC crack. The 16-inch O.D. pipeline was manufactured in 1961 from API 5LGrade X-52 steel, and was designed for and operates at a Maximum Allowable Operating Pressure (MAOP) of 896 psi. Second, a through-wall crack was found during a recent excavation in a 26-inch O.D. pipeline manufactured in 1956 from API 5L Grade X-52 steel, and operated at a MAOP of 832 psi.

FAD analysis and tearing instability assessment were then performed to estimate the critical crack size for the initiation of crack extension and leak-before-rupture. Assessments assumed that the cracks were single isolated cracks, i.e., no interactions between cracks in the crack field were considered. Prior to assessment, the material's true stress-strain curve, $J_{mat}$, and J-R curve were measured in accordance with ASTM standards E646, E833 and E1820 in order to perform high level FAD (material specific Method D) and tearing instability assessment.

Figure 7:
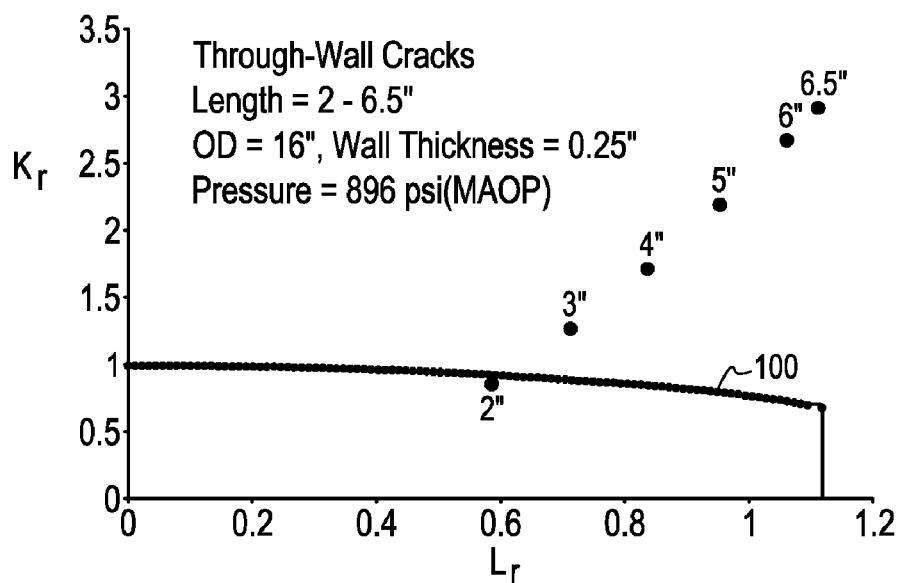
FIG. 7 is a level III assessment diagram showing critical crack sizes at a pressure of 896 psi (MAOP) in a 16 inch O.D. X-52 pipeline.

FIG. 7 shows the level III method-D assessment results (referred to API 579), indicating that through-wall cracks with a size larger than 2 inches are outside of the assessment curve 100 and not acceptable for service based on the crack initiation criteria.

Figure 8:
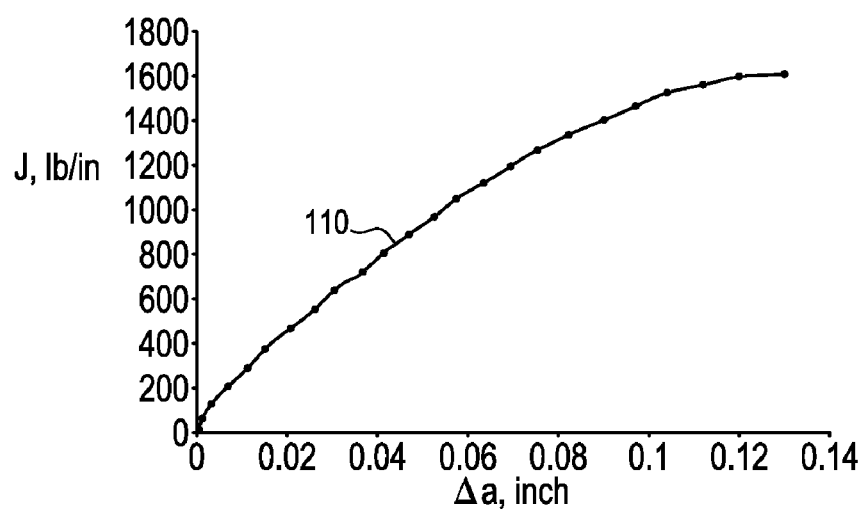
FIG. 8 is an actual J-R curve of a section cut out from the 16 inch O.D. pipeline in accordance with an exemplary embodiment.
Figure 9:
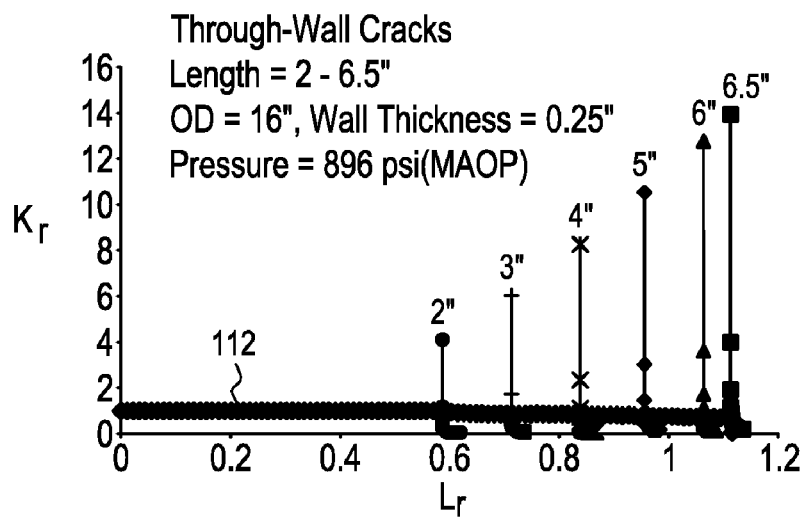
FIG. 9 is a FAD for ductile tearing analysis of different lengths of through-wall cracks in the 16 inch O.D. pipeline at MAOP 896 psi.

Tearing instability assessment showed, however, that through-wall cracks with a size smaller than 6.5 inches long would not result in catastrophic failure. FIG. 8 illustrates the measured J-R curve 110 and FIG. 9 illustrates a FAD ductile tearing analysis 112. In actuality, field examination found a small leak in 2001 and subsequent examination determined the size of the crack associated with the leak to be a 2.2-inch through-wall crack.

Figure 10:
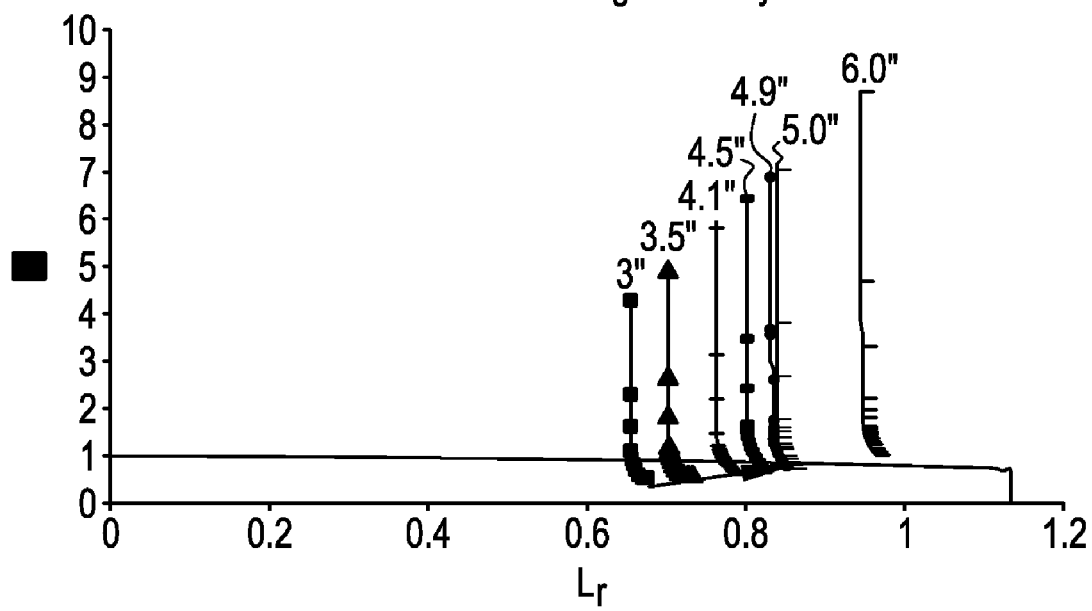
FIG. 10 is a FAD level III analysis for ductile tearing of different lengths of through-wall cracks in a 26 inch O.D. pipeline at MAOP 832 psi.

Similar assessment was performed on the 26-inch pipeline in the second example. Referring to FIG. 10, the ductile tearing analysis suggests that through-wall cracks with a size smaller than 4.9 inches would not cause rupture. The analysis is consistent with the field observation where a through-wall crack was found during excavation. The crack was a 3.6 inches long with part of the crack having penetrated through the wall. FIG. 10 illustrates the FAD analysis results.

The above analysis is based on an assumption of a single crack. However, cracks formed by SCC are often characterized as crack colonies or crack fields. Generally, SCC colonies are comprised of various crack sizes with inter-spacings therebetween. Fracture mechanics analysis suggests that failure initiates from one of the worst cracks caused by SCC and then links with others to form a larger crack that finally results in either a leak, rupture, or leak then rupture, depending on crack sizes, crack spacing, loading condition and material properties.

Figure 11:
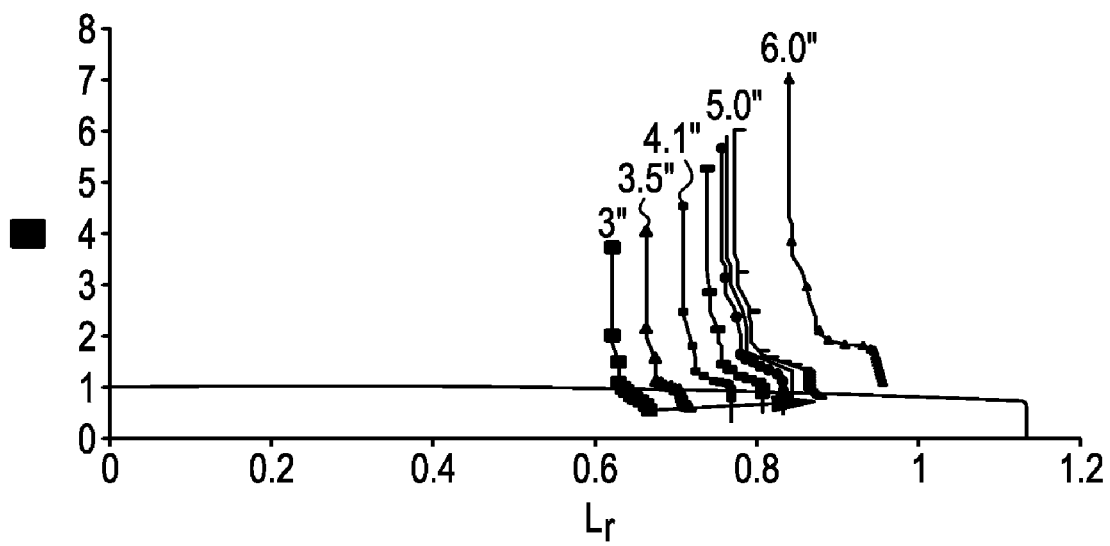
FIG. 11 is a FAD level III analysis for ductile tearing of different lengths of deep SSC cracks (i.e., 90% wt) of a colony in a X52 pipeline.

For example, if there is a very deep SCC crack (e.g., 90% wt) in a colony of SCC in a X52 pipeline, and the crack is longer than the critical size for initiation of extension but smaller than that for rupture in accordance with the FAD level III analysis, then this crack could start to grow by ductile tearing if a favorable loading condition (e.g., operating pressure) is present. The ductile tearing would predominantly occur at the deepest point of the crack where the stress intensity is the highest. The crack could readily penetrate through the remaining wall ligament and result in a leak. Rupture could finally occur as a result of linkage of this newly formed through-wall crack with its adjacent cracks to form a larger crack. Whether rupture occurs or not depends on the size of the linked cracks (for example, more than 4.5 inches long based on tearing instability analysis of FIG. 11) combined with local loading and temperature conditions (i.e. pressure fluctuation induced overload). The time for this transition, however, cannot be easily predicted—it could last for months, or several days, or hours. However, fractographic analysis for this particular case has shown that transition from leak to rupture might last a length of time in order to bring the temperature of the joint (about 15 ft from on either side of the fracture origin) down to the Charpy (CVN) transition temperature.

For shallow but closely aligned long cracks, (for example, crack depth<60% wt), inter-link of adjacent cracks is the main process for ductile tearing. Therefore, rupture is expected to be the predominant form for most of the failures of these types of cracks based on the tearing instability analysis.

The above described disclosure provides a leak-before-rupture criterion using a ductile tearing and tearing instability analysis approach. This criterion takes into account the significant ductile tearing and stable crack extension that may occur prior to catastrophic failure. Assessments based on this criterion provide more accurate predictions and are consistent with limited field examinations thus far. Preliminary results using this assessment criterion have shown that the chance for a leak-before-rupture in SCC induced crack-containing pipelines may not be low, for example, cracks with a depth of 90% wt and a length less than 4.5 inches will most likely leak before rupture for qualified X52 grade steel. These findings suggest that in addition to the current widely used "crack initiation based FAD analysis", a ductile tearing analysis should be used for integrity assessment if leak-before-rupture is a concern. The findings also suggest that the stress alone cannot predict a leak before rupture or vice-versa. A combined stress, material properties, temperature, and crack size determines the critical condition for failure by leak or rupture.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for leak-before-rupture assessment, the method comprising:
   using a failure assessment diagram (FAD) assessment curve from a crack initiation based FAD analysis to analyze a crack in a material; and
   using a ductile tearing analysis in conjunction with the FAD assessment curve to detect a crack exhibiting at least one of ductile tearing stability and tearing instability prone to rupture during growth of the crack;
   wherein the ductile tearing analysis takes into account an increase in a material fracture toughness during the crack growth.

2. The method of claim 1, further comprising:
   using a J-integral approach to describe an elastic-plastic fracture behavior of the material having the crack, wherein $J_{app}$=a driving force for a crack growth, and $J_{mat}$=a material resistance to the crack growth.

3. The method of claim 2, wherein the tearing instability criteria indicative of a rupture include $$J_{app} > J_{mat} \text{ and } \frac{\partial J_{app}}{\partial a} > \frac{\partial J_{mat}}{\partial a}.$$

4. The method of claim 3, wherein the crack growth is stable when $$J_{app} \leq J_{mat} \text{ and } \frac{\partial J_{app}}{\partial a} \leq \frac{\partial J_{mat}}{\partial a}.$$

5. The method of claim 4, wherein the ductile tearing analysis includes:
   plotting the FAD assessment curve;
   calculating a stress ratio ($L_r$) and a ratio of $$\sqrt{J_{app}/J_{mat}}$$

($K_r$) for a range of crack growth increments ($\Delta a$) corresponding to assessment points; and
   plotting the assessment points of Kr versus Lr for ductile tearing and tearing instability analysis.

6. The method of claim 5, wherein $L_r$ is a ratio of reference stress ($\sigma_{ref}$) to yield strength $$(\sigma_y)(\text{i.e., } \sigma_{ref}/\sigma_y), \text{ said } \sigma_{ref}$$

is a fraction of applied stress and crack size.

7. The method of claim 5, wherein said $J_{mat}$ is derived from a J-R curve for the material resistance to the range of crack growth increments ($\Delta a$).

8. The method of claim 7, wherein the J-R curve is experimentally established for the material at a temperature corresponding to an assessment temperature.

9. The method of claim 5, wherein said $J_{app}$ is calculated based on an applied load and a shape of the crack.

10. The method of claim 5, wherein when the assessment points fall below the FAD assessment curve, the crack growth is stable and will not rupture at a constant operating pressure or applied load.

11. The method of claim 5, wherein when all of the assessment points are disposed either above or tangent to the assessment curve, the crack growth is prone to failure by rupture at a constant operating pressure or applied load.

12. The method of claim 5, wherein when all of the assessment points are disposed entirely below the FAD assessment curve, the crack growth is not present at a constant operating pressure or applied load.

13. The method of claim 1, wherein the crack is one of a single crack and a crack field disposed in a pipeline.

14. A method to detect leak-before-rupture cracks in a pipeline material that exhibits stable crack growth by ductile tearing, the method comprising:

using a failure assessment diagram (FAD) assessment curve from a crack initiation based FAD analysis to analyze a crack in a material; and using a ductile tearing analysis in conjunction with the FAD assessment curve to detect a crack exhibiting at least one of ductile tearing stability and tearing instability prone to rupture during growth of the crack, wherein the ductile tearing analysis takes into account an increase in a material fracture toughness during the crack growth.

15. The method of claim 14, wherein the ductile tearing analysis includes:

plotting the FAD assessment curve;

calculating a stress ratio ($L_r$) and a ratio of $$\sqrt{J_{app}/J_{mat}}$$

($K_r$) for a range of crack growth increments ($\Delta a$) corresponding to assessment points; and plotting the assessment points of Kr versus Lr for ductile tearing and tearing instability analysis.

16. The method of claim 15, wherein $L_r$ is a ratio of reference stress ($\sigma_{ref}$) to yield strength $$(\sigma_y) (\text{i.e., } \sigma_{ref}/\sigma_y), \text{ said } \sigma_{ref}$$

is a function of applied stress and crack size.

17. The method of claim 15, wherein said $J_{mat}$ is derived from a J-R curve for the material resistance to the range of crack growth increments ($\Delta a$).

18. The method of claim 17, wherein the J-R curve is experimentally established for the material at a temperature corresponding to an assessment temperature.

19. The method of claim 15, wherein when the assessment points fall below the FAD assessment curve, the crack growth is stable and will not rupture at a constant operating pressure or applied load; when all of the assessment points are disposed either above or tangent to the assessment curve, the crack growth is prone to failure by rupture at a constant operating pressure or applied load; and when all of the assessment points are disposed entirely below the FAD assessment curve, the crack growth is not present at a constant operating pressure or applied load.

* * * * *

UNITED STATES PATENT AND TRADEMARK OFFICE
CERTIFICATE OF CORRECTION

PATENT NO.      : 7,039,528 B2
APPLICATION NO. : 10/710702
DATED           : May 2, 2006
INVENTOR(S)     : Ming Gao et al.

It is certified that error appears in the above-identified patent and that said Letters Patent is hereby corrected as shown below:

Column 1,
Line 30, after "a", delete "Level I" and insert therefor --Level II--.

Column 3,
Line 23, after "length", delete "a" and insert therefor --$a_o$--.
Line 24, after "at", delete "$a_i$" and insert therefor --$a_i$--.
Line 26, after "$\sigma_i$", insert --.--.
Line 36, after "length", delete "$a$" and insert therefor --a--.
Line 55, after "G" insert --$_{\sigma i}$--.
Lines 59-60, after "and", delete "$a$" and insert --a--.

Column 4,
Line 18, after "as", delete "J app" and insert therefor --Japp--.
Line 22, after "tearing", delete "instabilapp ity" and insert therefor --instability--.
Line 57, after "Δ", delete "$a$" and insert therefor --a--.
Line 58, after "length", delete "$a$" and insert therefor --a--.
Line 66, after "ratio", delete "L $_r$" and insert therefor --$L_r$--.

Column 5,
Lines 1-2, after "of", (second occurrence), delete "apref plied" and insert therefor --applied--.
Lines 8-9, after "(J-R)", delete "mat".
Line 9, after "Δ", delete "$a$" and insert therefor --a--.
Line 25, after "length", delete "$a$" and insert therefor --a--.

Column 6,
Line 6, after "that", delete "aJ-R" and insert therefor --a J-R--.

Column 7,
Line 20, after "crack", delete "depth<60%" and insert therefor --depth < 60%--.
Lines 41-42, after "or", delete "vice-versa" and insert therefor --*vice-versa*--.

UNITED STATES PATENT AND TRADEMARK OFFICE
CERTIFICATE OF CORRECTION

PATENT NO. : 7,039,528 B2
APPLICATION NO. : 10/710702
DATED : May 2, 2006
INVENTOR(S) : Ming Gao et al.

It is certified that error appears in the above-identified patent and that said Letters Patent is hereby corrected as shown below:

<u>Column 8,</u>
Line 44, after "a", delete "fraction" and insert therefor --function--.

Signed and Sealed this

Fifth Day of December, 2006

JON W. DUDAS
*Director of the United States Patent and Trademark Office*